(12) United States Patent
Seward

(10) Patent No.: US 6,565,526 B2
(45) Date of Patent: May 20, 2003

(54) BISTABLE MICROVALVE AND MICROCATHETER SYSTEM

(75) Inventor: Kirk Patrick Seward, Dublin, CA (US)

(73) Assignee: The Regents of the University of California, Oakland, CA (US)

( * ) Notice: Subject to any disclaimer, the term of this patent is extended or adjusted under 35 U.S.C. 154(b) by 125 days.

(21) Appl. No.: 09/802,211

(22) Filed: Mar. 8, 2001

(65) Prior Publication Data

US 2002/0013555 A1 Jan. 31, 2002

Related U.S. Application Data

(60) Provisional application No. 60/188,330, filed on Mar. 9, 2000.

(51) Int. Cl.[7] .................. A61M 31/00; F16K 31/00; F16K 15/14
(52) U.S. Cl. .................. 604/93.01; 251/11; 137/859
(58) Field of Search .................. 604/93.01, 244, 604/245, 246, 247, 264, 523, 536, 537, 500, 508; 251/11, 82; 137/859

(56) References Cited

U.S. PATENT DOCUMENTS

| | | | | |
|---|---|---|---|---|
| 5,325,880 A | * | 7/1994 | Johnson et al. | 137/1 |
| 5,619,177 A | | 4/1997 | Johnson et al. | 337/140 |
| 5,634,913 A | | 6/1997 | Stinger | 604/272 |
| 5,659,171 A | | 8/1997 | Young et al. | 250/289 |
| 5,762,630 A | * | 6/1998 | Bley et al. | 604/164.01 |
| 5,771,902 A | * | 6/1998 | Lee et al. | 128/897 |
| 5,819,749 A | * | 10/1998 | Lee et al. | 128/899 |
| 5,833,706 A | | 11/1998 | St. Germain et al. | 606/194 |
| 6,102,897 A | * | 8/2000 | Lang | 604/246 |
| 6,102,917 A | * | 8/2000 | Maitland et al. | 606/108 |

FOREIGN PATENT DOCUMENTS

| | | | | |
|---|---|---|---|---|
| WO | WO 99/38551 | 8/1999 | | A61M/5/142 |
| WO | WO 99/39118 | 8/1999 | | F16K/7/04 |
| WO | WO 99/44666 | 9/1999 | | A61M/25/00 |

OTHER PUBLICATIONS

C. Goll, et al., "Microvalves with bistable buckled polymer diaphragms," J. Micromech. Microeng. 6 (1996) pp. 77–79.
T. Lisec, et al., "A bistable pneumatic microswitch for driving fluidic components," Sensors and Actuators A 54, Elsevier Science S.A., (1996) pp. 746–749.
H. Tobushi, et al., "Thermomechanical Constitutive Modeling in Shape Memory Polymer of Polyurethane Series," Journal of Intelligent Material Systems and Structures, vol. 8, Aug. 1997, pp. 711–718.
H. Tobushi, et al., "Mechanical Properties of Shape Memory Polymer of Polyurethane Series (Basic Characteristics of Stress–Strain–Temperature Relationship)," JSME International Journal, Series 1, vol. 35, No. 3, 1992, pp. 296–302.

* cited by examiner

Primary Examiner—Edward K. Look
Assistant Examiner—John K Fristoe, Jr.
(74) Attorney, Agent, or Firm—Eddie E. Scott; Alan H. Thompson

(57) ABSTRACT

A bistable microvalve of shape memory material is operatively connected to a microcatheter. The bistable microvalve includes a tip that can be closed off until it is in the desired position. Once it is in position it can opened and closed. The system uses heat and pressure to open and close the microvalve. The shape memory material will change stiffness and shape when heated above a transition temperature. The shape memory material is adapted to move from a first shape to a second shape, either open or closed, where it can perform a desired function.

14 Claims, 6 Drawing Sheets

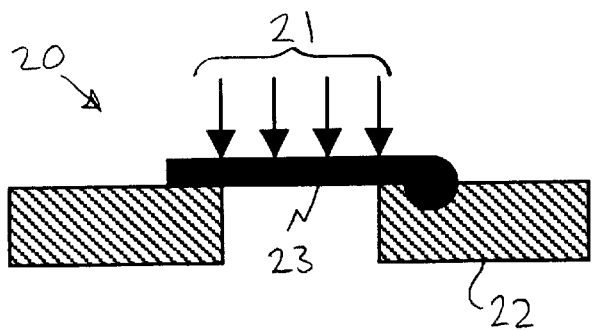
FIG. 4 A
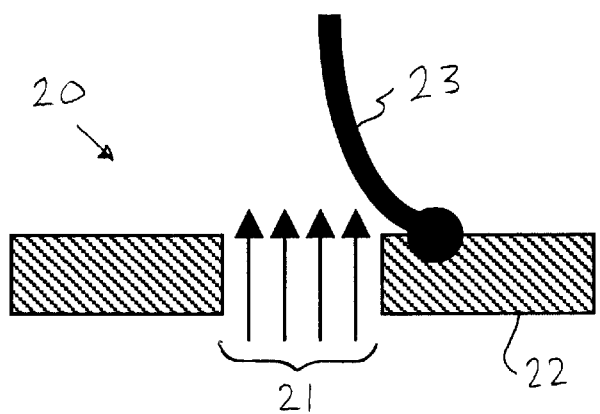
FIG. 4 B
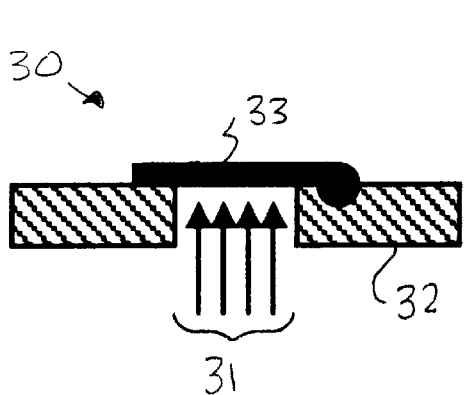
FIG. 5 A
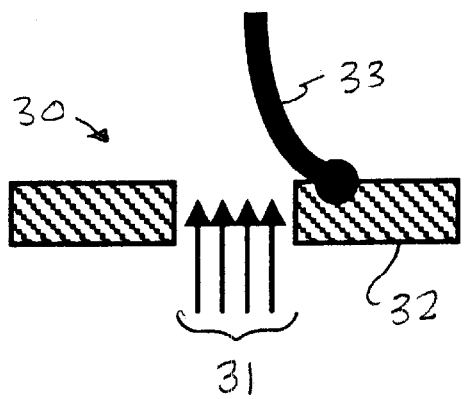
FIG. 5 B

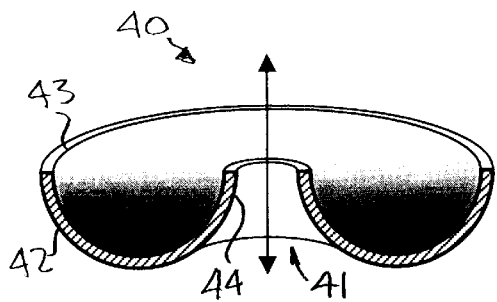
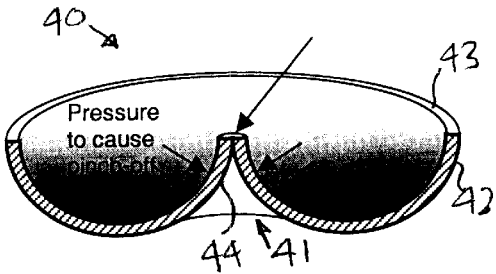
FIG. 6A  FIG. 6B
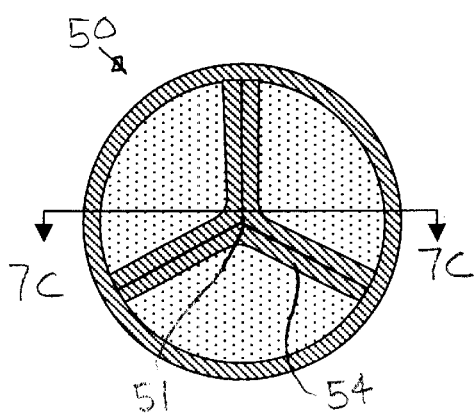
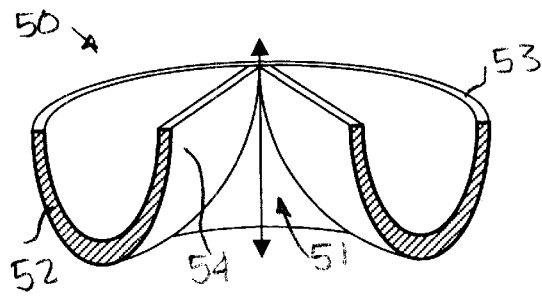
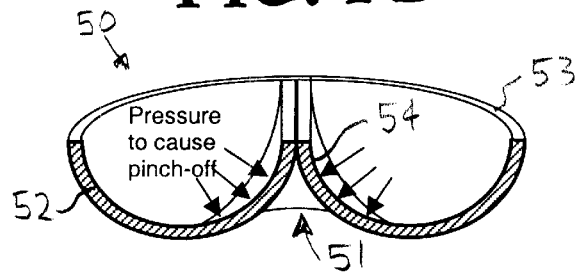
FIG. 7A  FIG. 7B
FIG. 7C
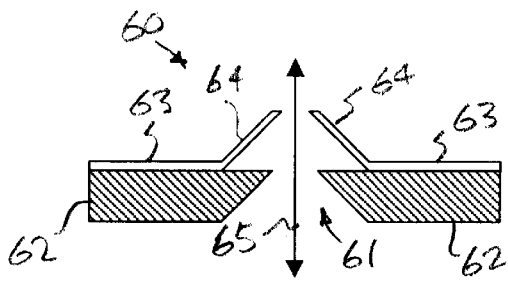
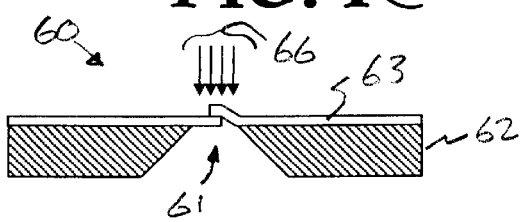
FIG. 8A  FIG. 8B

BISTABLE MICROVALVE AND MICROCATHETER SYSTEM

CROSS-REFERENCE TO RELATED APPLICATIONS

This application claims the benefit of U.S. Provisional Application No. 60/188,330, filed Mar. 9, 2000, and entitled "A Bistable Microvalve for Use with Microcathers," which is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of Endeavor

The present invention relates to microvalves and more particularly to microvalves for use with microcatheters.

2. State of Technology

Microcatheters are used in many medical applications for minimally invasive surgery. It is estimated there are presently over 700,000 surgical uses of catheters per year in the United States representing a market of over $350 million. They can in inserted into arteries or veins and snaked around within the body until their tip is in a desired location. Catheter type devices are also used with minimally invasive techniques including biomonitoring, biosensing and nuclear stockpile monitoring.

U.S. Pat. No. 5,819,749 for a microvalve by Abraham Lee, et al, patented Oct. 13, 1998 provides the following description: "Present catheter technology, while significantly improving the outcome of severe trauma and congenital diseases is lacking in technological sophistication. Specifically, catheters lack sub-millimeter-sized distal actuators and sensors, adequate embolic and stenting materials and devices, feedback control (both force and tactile), computer-based autonomous control of steering and actuation, and sufficient imaging/therapy coupling. Presently, the catheter-based procedures for cardiological, neurological, and peripheral vessel repairs and treatments require direct, hands-on, continuous manipulation by experienced physicians. Procedures, especially in the neurological field, can be very lengthy (4–6 hours) and extremely tedious. Some improvements have been made in catheter technology for access; i.e., getting to the site of therapy. Examples are new guidewire materials and reduced sizes of the catheters. As well, there have been new innovations in therapies, especially in the cardiology field. These include balloon angioplasty, laser ablation, stenting, and rotobladers. Most of these are specifically designed to treat arteriosclerosis, and have been minimally successful (restenosis rates of over 35% are common). Most intravascular therapies that are potentially deliverable by catheter methodology are severely limited by the lack of sophistication of the tools themselves, the control of the tools, and the associated technologies such as imaging. By improving and miniaturizing the distal end tools (microtools), providing force and tactile feedback, integrating sensors and autonomous steering, and improving imaging (optical and ultrasound); this very powerful medical technology will be made more usable, widespread, and efficient."

U.S. Pat. No. 5,325,880 for a shape memory alloy film actuated microvalve by David Johnson, patented Jul. 5, 1994, provides the following description in its abstract: "A sub-miniature valve which provides an actuator of shape memory alloy film coupled so as to move a poppet adjacent to a valve port. The shape memory alloy film actuator is thermally cycled through its phase change transition temperature, resulting in either a contraction or elongation of the actuator. This causes the poppet to move relative to the port and either increase or decrease fluid flow. The shape memory alloy film is biased toward its deformed position when cooled below its transition temperature. The valve can be electrically operated with commonly available voltages, including those used for micro-electronics. The relatively large forces and displacements achieved using the shape memory alloy film provide less restriction and greater flow than in other similarly sized valves."

World Intellectual Property Organization Patent No. WO9938551 for an implantable drug infusion device having a safety valve, published Aug. 5, 1999, by Koen Weijand, et al, provides the following description: An implantable drug infusion device which features a safety valve. The safety valve is normally in the closed state and only opens upon electrical activation. The valve is designed so as to be constructed in an extremely small size and further to be made of corrosion resistant materials. The valve may be used in either a passive or an active drug infusion system. Also disclosed is an efficient circuit to drive, i.e. open and close, the safety valve. Further disclosed is a timing scheme for opening and closing the safety valve for use in an active drug infusion device.

U.S. Pat. No. 5,634,913 for a softening conduit for carrying fluids into and out of the human body by Florence Stinger, patented Jun. 3, 1997 provides the following description: "In the field of catheters, it has been proposed to utilize a polymer material which softens at body temperature and/or upon exposure to moisture. Such catheters are disclosed, for example, in U.S. Pat. Nos. 4,846,812 and 5,441,489, and comprise a rigid portion for manipulation of the catheter and a portion which becomes flexible after insertion into the body. This flexibility can be delayed for a period of time to enable the catheter to be properly positioned. However, when puncturing of the skin is necessary, it is still necessary to make an incision or to puncture the skin with a separate lancet. For example, U.S. Pat. Nos. 4,883,699 and 4,911,691 disclose a catheter formed of a polymer which softens upon absorbing water used in combination with a metal lancet which passes therethrough for puncturing the skin. U.S. Pat. No. 4,955,863 similarly discloses a catheter assembly including a cannula, a needle and a catheter inserter in slidable relationship to the cannula. These devices present the disadvantage that metal lancets are necessary, presenting the safety and disposal problems discussed above. Further, the lancet or guidewire used in connection with the catheter is necessarily longer than the catheter itself, and enters the body first, at which time the practitioner must push the lancet or guidewire further in order to correctly position the catheter. This procedure is a risk to the patient, as the lancet or guidewire may puncture a vessel, membrane, tendon, bone, nerve, lung or spinal cord. Early detection of the appropriate placement of the catheter is not possible with these devices combining a metal lancet or guidewire with a catheter."

U.S. Pat. No. 6,102,917 for a shape memory polymer (SMP) gripper with a release sensing system, by Maitland et al, patented Aug. 15, 2000, and assigned to provides the following description: "A system for releasing a target material, such as an embolic coil from an SMP located at the end of a catheter utilizing an optical arrangement for releasing the material. The system includes a laser, laser driver, display panel, photodetector, fiber optics coupler, fiber optics and connectors, a catheter, and an SMP-based gripper, and includes a release sensing and feedback arrangement. The SMP-based gripper is heated via laser light through an optic fiber causing the gripper to release a target material (e.g., embolic coil for therapeutic treatment of aneurysms). Various embodiments are provided for coupling the laser light into the SMP, which includes specific positioning of the coils, removal of the fiber cladding adjacent the coil, a metal coating on the SMP, doping the SMP with a gradient absorbing dye, tapering the fiber optic end, coating the SMP with low refractive index material, and locating an insert between the fiber optic and the coil." U.S. Pat. No. 6,102,917 is incorporated herein in its entirety by reference.

SUMMARY OF THE INVENTION

The present invention provides a valve system for catheters and catheter type devices used with minimally invasive techniques such as biomonitoring, biosensing, nuclear stockpile monitoring, chemical delivery systems, and surgical procedures. In one embodiment of the present invention, a bistable microvalve system is provided for use with microcatheters. A bistable microvalve of shape memory material is operatively connected to a microcatheter. The bistable microvalve includes a tip that can be closed off until it is in the desired position. Once it is in position it can opened and closed. The system uses heat to activate the shape memory material. The shape memory material's elastic modulus will change when heated above a transition temperature. The shape memory material is adapted to move from a first shape to a second shape, either open or closed, where it can perform a desired function. Other features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description and by practice of the invention.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIGS. 4A and 4B show a standard check valve illustrating the opening or closing based on direction of pressure gradient across fluidic port.

FIGS. 5A, 5B, 5C, 5D, 5E, 5F, 5G, and 5H illustrate the opening and closing of a bistable SMP variable-modulus check valve.

FIGS. 6A and 6B show a cross-sectional view of a semi-toroidal catheter tip microvalve in an opened and closed state.

FIGS. 7A, 7B, and 7C show plan and cross-sectional views of a tricuspid catheter tip microvalve in an opened and closed state.

FIGS. 8A and B show micro electromechanical systems (MEMS) based microvalve made from molded SMP attached to a micromachined substrate.

DETAILED DESCRIPTION OF THE INVENTION

Figure 1:
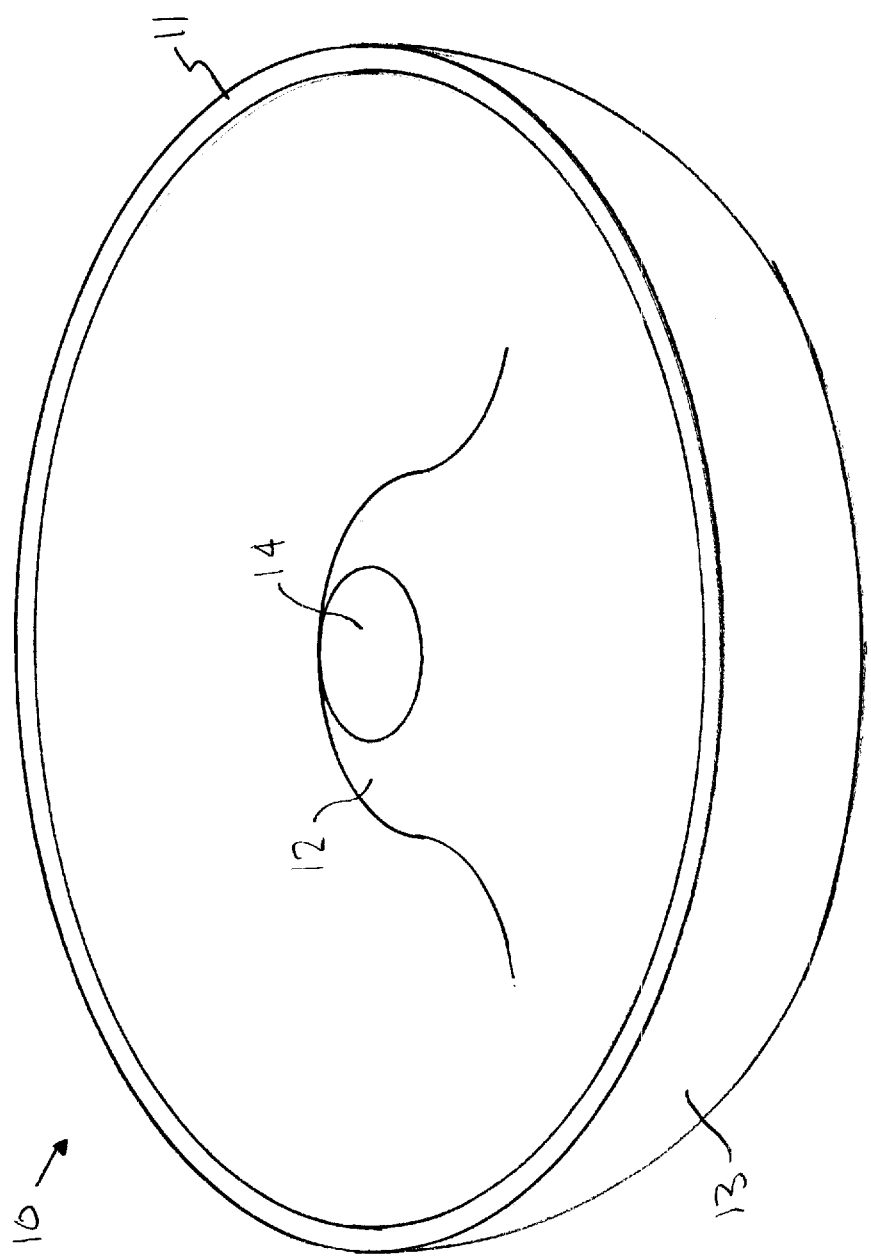
FIG. 1 shows an embodiment of a bistable microvalve.
Figure 2A:
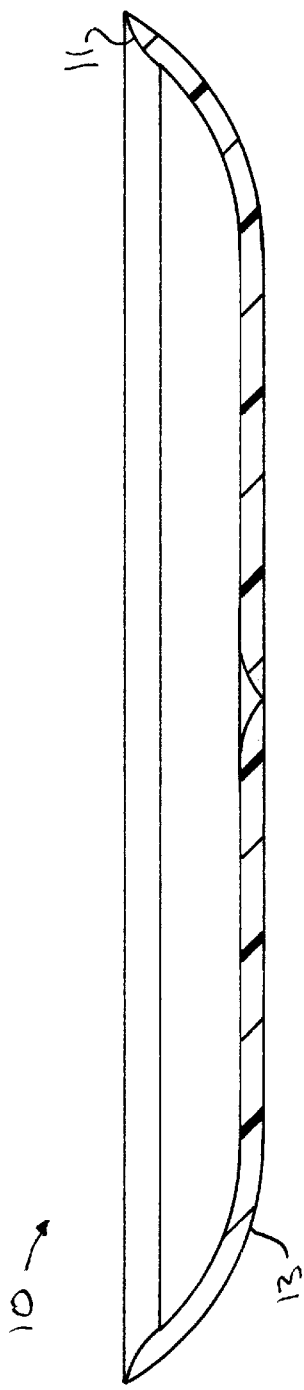
FIG. 2A is a sectional view of the bistable microvalve in its closed position.
Figure 2B:
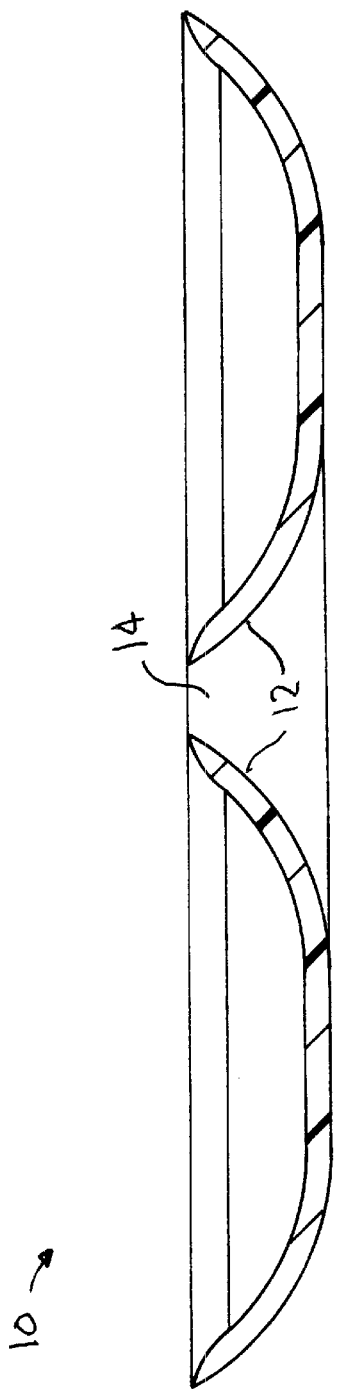
FIG. 2B is a sectional view of the bistable microvalve in its open position.

Referring now to the drawings, specific embodiments of the invention are shown. The detailed description of the specific embodiments, together with the general description of the invention, serves to explain the principles of the invention. The present invention provides a valve system used for catheters and catheter type devices used with minimally invasive techniques such as biomonitoring, biosensing, nuclear stockpile monitoring, chemical delivery systems, and surgical procedures.

The bistable valve and catheter or catheter like apparatus includes a catheter or catheter like device. A bistable valve body is operatively connected to the catheter or catheter like device. The bistable valve body has a passage and is at least partially made of a shape memory material such as a shape memory polymer (SMP) adapted to move from a first shape where the passage is restricted or closed to a second and different shape where the passage is open. The shape memory polymer material possesses a glass transformation temperature ($T_g$) above which the material enters its rubbery state where it becomes soft and flexible and easy to reshape the material and will return to its primary shape if not subjected to excessive loading. Once cooled below $T_g$, the shape is frozen in place by the material's glassy state and the material becomes hardened and will hold its shape until it is intentionally relaxed by heating the SMP above $T_g$.

A heat transfer mechanism is operatively connected to the shape memory material. These systems include induced resistive heating by an external wave field, such as by an associated magnetic or radio frequency (RF) source, external heating through electrical induction or electrothermal heating, with local or remote ultrasonics or other acoustic means of energy transfer, or by converting optical energy into thermal energy that allows the stored energy in the shape memory material to be released. The heating of the SMP can be accomplished by an operatively connected or embedded mechanism which is powered by the absorption of applied energy in the form of light, electric fields, magnetic fields, RF fields, electromagnetic waves, acoustic/ ultrasound waves, electric current flow (DC: resistive heating, AC: inductive or dielectric heating), chemical reactions and/or other heating mechanisms such as nuclear heating etc. The optical energy is absorbed by the shape memory material and converted into thermal energy that heats the shape memory material above its transition temperature and the shape memory material moves to its primary shape, resulting in opto-mechanical actuation. Also, the shape memory material can be heated as described in U.S. Pat. No. 5,911,737 for microfabricated therapeutic actuators, by Lee et al, patented Jun. 15, 1999 as follows: "Heating of the SMP tubing can be accomplished via induced resistive heating of the end of object by an external wave field, such as by an associated magnetic or radio frequency (RF) source, provided of cause that the end of object is constructed of material inductive of resistance heating. External heating of the end of object can be carried out through electrical induction or electrothermal heating (through a dielectric lossy material on the end of the coil).

An example is by applying an external alternating magnetic field to Ni—Pd material coated on at least the end of object or coil." The disclosure of U.S. Pat. No. 5,911,737 is incorporated herein by reference. The shape memory material can also be heated using an optical system. The system uses energy in the form of light guided by an optical fiber to a light, diffusing device that radiates the light into the shape memory material. The light is absorbed by the shape memory material and converted into heat.

Application of heat to the SMP flap portion of the bistable valve causes the flap portion to be varied between soft and stiff. In operation, the bistable valve can be held open or closed by the stiffness of the flap. The bistable valve will only open or close during applied heat and pressure. Raising the temperature of the SMP above the glass transition temperature softens the material and allows it to easily deform under the pressure around it. If the applied pressure remains and the heat source is removed, the SMP becomes rigid and holds the shape that was imposed by the pressurization. When pressure is removed, the SMP structure tends to hold a similar shape, thus keeping the valve opened or closed. Reversing the pressure bias while the SMP is rigid will not reverse the opened or closed state of the valve.

The structural elements of the bistable valve and catheter or catheter like apparatus having been described, the operation of system will now be considered. The present invention provides a method of transmitting a material through a vessel or conduit. A catheter or catheter like conduit is provided. A bistable valve is attached to the catheter or conduit. The valve has a central passage. The valve includes a shape memory material flap portion adapted to move from a first shape wherein the passage is restricted or closed to a second and different shape wherein the passage is open. The catheter and valve are moved through the vessel or conduit. Heat and pressure can be transmitted to the shape memory material flap portion of the valve to cause the shape memory material flap portion to move from a first shape wherein the passage is restricted or closed to a second and different shape wherein the passage is open. For example, heat can be transmitted to the shape memory polymer material by transmitting light through an optical fiber and allowing the light energy to heat the shape memory polymer material. The shape memory polymer material possesses a glass transformation temperature ($T_g$) above which the material enters its rubbery state where it becomes soft and flexible and easy to reshape the material and will return to its primary shape if not subjected to excessive loading. Once cooled below $T_g$, the shape is frozen in place by the material's glassy state and the material becomes hardened and will hold its shape until it is intentionally relaxed by heating the SMP above $T_g$. The material can then be transmitted through the valve either into or out of the catheter or conduit. When the valve is open and the gauge pressure is positive inside the catheter or conduit, fluid flows out through the valve. When the valve is open and the gauge pressure is negative inside the catheter or conduit, fluid flows into the catheter or conduit.

The present invention can be used in many medical applications and various minimally invasive techniques such as biomonitoring, biosensing, nuclear stockpile monitoring, and chemical delivery systems. The catheter or conduit and bistable valve can be inserted into passages and snaked around until the bistable valve is in a desired location. Once the bistable valve is in the desired location numerous procedures can be accomplished. These procedures include controlled release of a substance into the desired location, collection of a sample from the desired location, sensing of changes in conditions at the bistable valve, or imaging through endoscopic fibers. In each of these cases, necessity requires that the tip of the catheter or conduit must be closed off until it is in position, at which point it is to be readily opened and closed.

FIG. 1 illustrates an embodiment of a bistable microvalve used with a microcatheter. This embodiment of the bistable microvalve can best be described as looking like a tiny sombrero with a hole in the middle (or one half of a hollow torus). When the valve is attached to the end of a microcatheter, as shown in the cross-sectional drawings of FIGS. 3A and 3B, the microvalve and microcatheter can be used for controlled release of a substance into the desired location or the collection of a sample from the desired location. When the valve is open and the gauge pressure is positive inside the catheter, fluid can flow out of the catheter through the valve. When the valve is open and the gauge pressure is negative inside the catheter, fluid can flow into the catheter. Microcatheters are used in many medical applications for minimally invasive surgery. They can be inserted into arteries or veins and snaked around within the body until their tip is in a desired location, at which point one of several things could happen. This includes imaging through endoscopic fibers, sensing of changes in tip conditions, or controlled release of a substance into the bloodstream. In each of these cases, necessity states that the tip of the catheter tube must be closed off until it is in position, at which point it can be readily opened and closed. The present invention provides the opening and closing of the catheter tip using heat from a fiber optic laser in the catheter and pressure from pressurized fluid, i.e., saline in the catheter.

With the large advent of microcatheter use in surgical procedures, the problem has arisen of how to control fluid flow at the distal end (the end in the body) of the catheter. Currently, valves are used on the outside of the body to control fluid dispensation at the tip of the catheter and large dead volumes of fluid are encountered, leading to poor flow control. Placing a valve at the distal end of the catheter would improve the accuracy of flow control and therefore increase the success rate of these surgical procedures.

Other problems have arisen from biosensing and biomonitoring applications. One particular application involves a sensor located on the tip of a fiber optic cable that is inserted into the body to a desired location through a catheter tube. The sensor is "one-shot" and can therefore not be exposed to blood until it is at the desired location. The distal end of the catheter must therefore be closed until the fiber is in place, at which point it should open. A bistable valve would allow for the measurement to be taken, after which the catheter could be flushed of all blood, the valve could be closed, and another fiber could be inserted to make further measurements.

The bistable valve presented here addresses the problem of large dead volumes by closing off the distal end of the catheter. It allows multiple measurements to be made by sensors without exposure until the desired position is reached. It also solves another problem seen in the invention description by eliminating the need for electronics to be placed inside the catheter to produce actuation. Since it is actuated by heating, a fiber optic laser placed inside the catheter can produce the necessary power to allow actuation and the opening or closing the valve. Shape memory polymer can be utilized as the material in this invention because it is biocompatible.

The bistable valve employs the properties of shape memory polymer (SMP) for actuation. This material is stiff at ambient temperature and soft when heated above its glass transition temperature Tg. The material experiences a modulus change of two orders of magnitude, which allows it to hold a shape while cold and deform easily while hot. The SMP also has the shape memorizing property of being able to return to its originally molded shape upon heating in the absence of external loads.

Figure 3B:
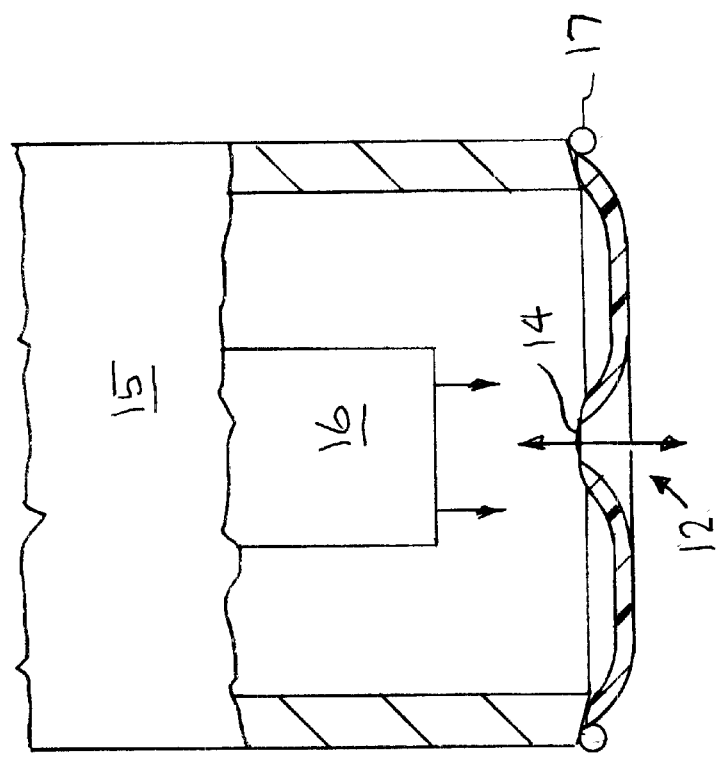
FIGS. 3A and 3B show the bistable microvalve operatively connected to a microcatheter and optical fiber.
Figure 3A:
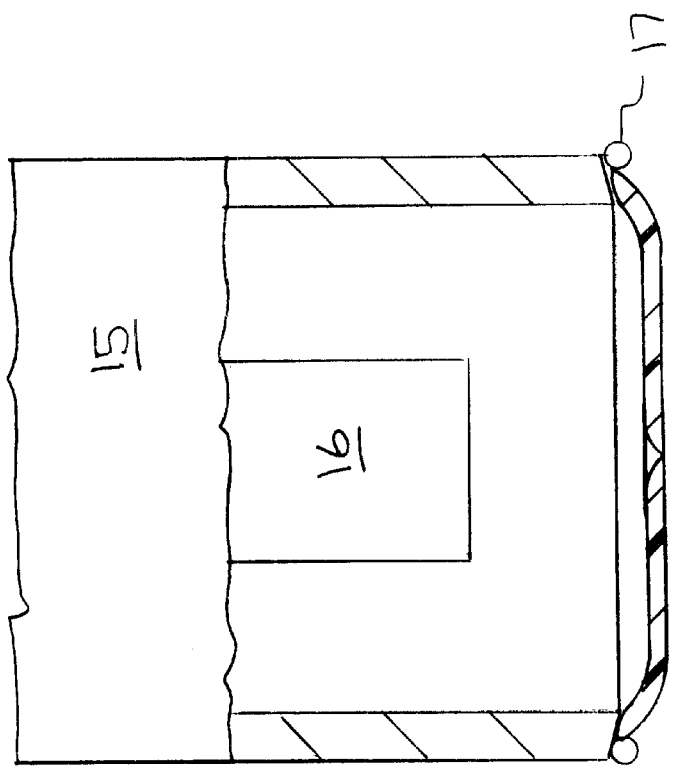

The structural elements of one embodiment of the bistable microvalve and microcatheter will now be described with reference to FIGS. 1, 2A, 2B, 3A, and 3B. The microvalve, generally designated by the reference numeral 10, looks like a tiny sombrero with a hole 14 in the middle (or one half of a hollow torus). The microvalve 10 has an outer wall 13 that forms a ridge 11. The microvalve 10 also has an inner wall 12 adjacent the hole 14. When the valve 10 is attached to the end of a microcatheter 15, as seen in the cross-sectional drawings of FIGS. 3A and 3B, actuation is can be accomplished. When the valve 10 is open and the gauge pressure is positive inside the catheter 15, fluid can flow out of the catheter 15 through the valve 10. When the valve is open and the gauge pressure is negative inside the catheter, fluid can flow into the catheter. When pressure is lowered inside the catheter 15, fluid flows into the catheter 15 through the valve 10. To actuate the microvalve 10, the SMP is heated with an accompanying pressure difference between the outside and inside of the valve 10. The valve 10 is closed by heating the inner wall 12, which is constructed of a shape memory polymer (SMP). The heating can be accomplished using any of the previously described systems. As shown in FIGS. 3A and 3B, heating is accomplished with a fiber optic laser 16. The pressure inside the catheter 15 is raised. This causes the inner wall 12 of the valve inlet to collapse upon itself, sealing against fluid flow. The laser is then turned off while pressure is still raised in order to set the polymer in its low temperature state. The valve 10 is now stable in its closed position. To open the valve 10, the SMP is once again heated by the laser and the pressure inside the catheter 15 is lowered. This forces fluid through the valve port 14, pulling it open. When the laser is turned off again, the valve 10 is locked into its open position.

These tiny valves can be fabricated using microfabrication techniques on glass and silicon wafers to make a mold cavity or precision machining techniques to make micromolds, into which SMP is molded and cured. Using these methods, valves can be made of varying thickness down to the order of 10 microns and varying diameter to fit onto the end of any catheter. A retainer ring 17 is utilized to hold the SMP valve 10 onto the end of the catheter 15.

The optical fiber 16 can be used as a diagnostic sensor at the distal tip of the catheter 15. Since the method-of-use includes pushing the device through a vessel, a sensor on the distal tip of the catheter 15 allows for the interrogation of the environment at the end of the catheter 15. In medical applications, for example, this could provide a useful diagnostic tool. The sensor is light based. The use of multiple wavelengths and wavelength-specific reflective coatings would enable the device to keep the heating wavelength(s) confined to the SMP material and allow diagnostic wavelengths to pass to the distal tip and back. Alternatively, the same wavelength(s) may be used for both actuating the SMP and interrogating the diagnostic end. In this case, instrumentation techniques like heterodyne detection, interference, or fluorescence may be useful in isolating the optical changes at the distal tip.

A better understanding of the present invention can be obtained by reviewing the fundamental aspects of a standard check valve. FIGS. 4A and 4B show a standard check valve, generally designated by the reference numeral 20, illustrating the opening or closing based on the direction of pressure gradient 21 across fluidic port. The standard check valve 20 will occlude flow in one direction and allow it in the other direction. A pressure drop across the fluidic port will tend to push the flap 23 over the port or out of the way of the port depending on the direction of pressurization 21 as shown in FIGS. 4A and 4B. The flap 23 is attached to the body 22 of the valve 20. The valve 20 is closed as shown in FIG. 4A when pressure 21 forces the flap 23 against the valve body 22 blocking the fluidic port. The valve 20 is opened as shown in FIG. 4B when pressure 21 forces the flap 23 away from the valve body 22 opening the fluidic port.

An understanding of the present invention can be obtained by considering the fundamental aspects of a bistable SMP variable-modulus check valve. FIGS. 5A, 5B, 5C, 5D, 5E, 5F, 5G, and 5H illustrate fundamental aspects of the opening and closing of a bistable SMP variable-modulus check valve, generally designated by the reference numeral 30. The valve 30 includes a flap 33 constructed of shape memory polymer (SMP) materials. The flap 33 is connected to the body 32 of the valve 30 and adapted to move from an open position to a closed position.

Figure 5C:
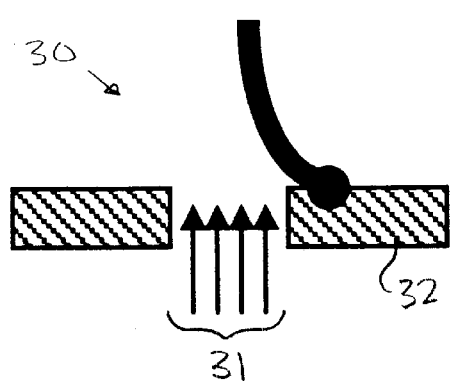
Figure 5D:
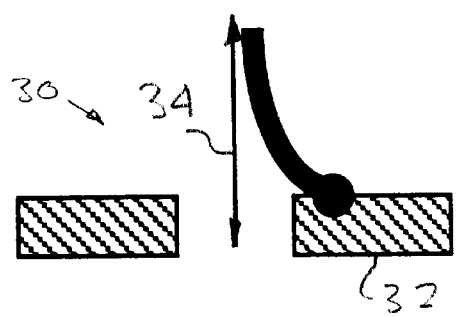

In FIG. 5A, the flap is shown in a closed position. Pressure 31 alone will not open the valve 30. In FIG. 5B the valve 30 is shown in the open position. Pressure plus heating of the SMP flap 33 opens the valve 30 by softening the SMP material and allowing pressure 31 to move the flap 33 to the open position. In FIG. 5C the valve 30 remains in the open position. Removal of the heat while the pressure 31 remains freezes the SMP flap 33 in the open position shape. As shown in FIG. 5D with the flap 33 frozen in the open position shape, flow 34 can occur in either direction. This allows controlled release of a substance into a desired location or the collection of a sample from a desired location.

Figure 5E:
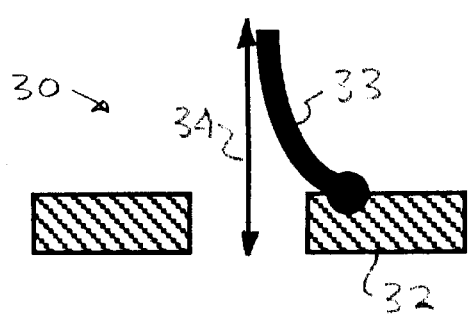
Figure 5F:
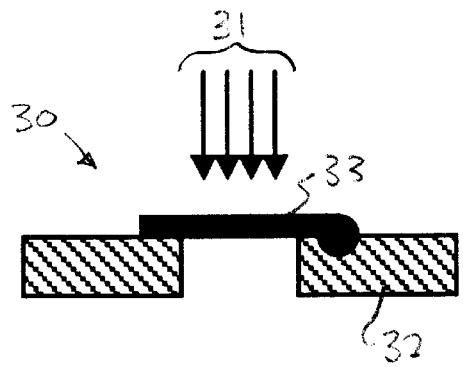
Figure 5G:
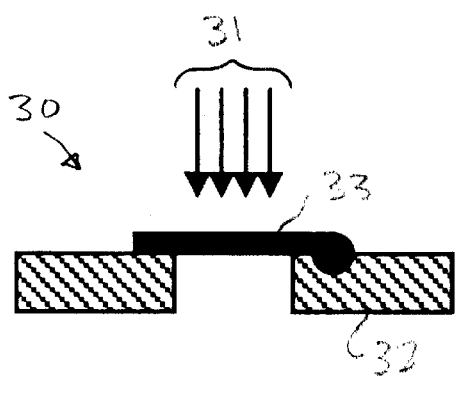
Figure 5H:
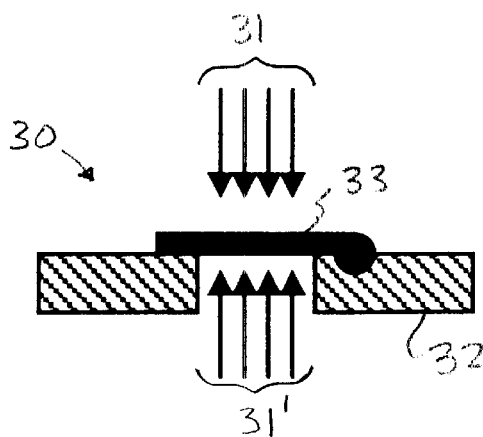

The opening of the valve 30 having been described with reference to FIGS. 5A through 5D, the closing of the valve 30 will now be described with reference to FIGS. 5E through 5H. As shown in FIG. 5E with the flap 33 frozen in the open position shape, flow 34 can occur in either direction. Pressure plus heating of the SMP flap 33 closes the valve 30 by softening the SMP material and allowing pressure 31 to move the flap 33 to the closed position as shown in FIG. 5F. Removal of the heat while the closing pressure 31 remains freezes the SMP flap 33 in the closed position shape as shown in FIG. 5G. As shown in FIG. 5H the frozen shape of flap 33 occludes flow 31 and flow 31' in both directions with the valve 30 held shut.

The bi-stability arises from the valve's operation as a variable modulus check-valve. The modulus of the flap 33 shown in FIGS. 5A, 5B, 5C, 5D, 5E, 5F, 5G, and 5H can be varied between soft and stiff by an elastic modulus change of more than two orders of magnitude. When heat is applied to the SMP the check valve 30 can be held open or closed by the stiffness of the flap 33. The check valve 30 will only open or close during applied heat and pressure. Raising the temperature of the SMP above the glass transition temperature softens the material and allows it to easily deform under the pressure around it. If the applied pressure remains and the heat source is removed, the SMP becomes rigid and holds the shape that was imposed by the pressurization. When pressure is removed, the SMP structure tends to hold a similar shape, thus keeping the valve opened or closed. Reversing the pressure bias while the SMP is rigid will not reverse the opened or closed state of the valve.

The bistable SMP variable-modulus check valve described in connection with FIGS. 5A, 5B, 5C, 5D, 5E, 5F, 5G, and 5H provides a bistable valve and catheter (or conduit) system that includes a conduit and a bistable valve body operatively connected to the conduit and optical fiber in the same manner as that shown in FIGS. 3A and 3B. The bistable valve body 32 has a passage that can be blocked by the flap 33. The flap 33 includes a shape memory material adapted to move from a first shape wherein said passage is restricted or closed to a second and different shape wherein said passage is open. Once the bistable valve is in the desired location numerous procedures can be accomplished. The bistable SMP variable-modulus check valve described in connection with FIGS. 5A, 5B, 5C, 5D, 5E, 5F, 5G, 5H, and 3A and 3B can be used in many medical applications and various minimally invasive techniques such as biomonitoring, biosensing, nuclear stockpile monitoring, and chemical delivery systems. The term catheter is understood to include various conduit applications wherein the bistable valve and conduit can be in inserted into passages and snaked around until the bistable valve is in a desired location. These applications include controlled release of a substance into the desired location, collection of a sample from the desired location, sensing of changes in conditions at the bistable valve, or imaging through endoscopic fibers. In each of these cases, necessity requires that the tip of the catheter or conduit must be closed off until it is in position, at which point it is to be readily opened and closed. The term catheter as used in this specification and the claims includes all conduit applications.

Referring now to FIGS. 6A and 6B, an embodiment of the invention is shown consisting of a hollow semi-toroidal structure in which the hole through the center is the fluidic port. FIGS. 6A and 6B show a microvalve, generally designated by the reference numeral 40 with a fluidic port 41 in the middle. The microvalve 40 has an outer wall 42 that forms a ridge 43. The microvalve 40 also has an inner wall 44 adjacent the fluidic port 41. The inner wall is constructed of a shape memory polymer (SMP).

The valve 40 is adapted to be attached to the end of a microcatheter as described earlier. When pressure is raised inside the catheter, fluid can flow out of the catheter through the valve 40 and when pressure is lowered inside the catheter fluid can flow into the catheter through the valve 40 as shown by the double headed arrow.

To actuate the microvalve 40, the SMP is heated with an accompanying pressure difference between the outside and inside of the valve 40. The valve 40 is closed by heating the inner wall 44, which is constructed of a shape memory polymer (SMP). The pressure inside the catheter is raised. This pressure causes the inner wall 44 of the valve to pinch-off sealing against fluid flow. The heat is then raised while pressure is still raised in order to set the polymer in its low temperature state. The valve 40 is now stable in its closed position. To open the valve 40, the SMP is once again heated and the pressure inside the catheter is lowered. This forces fluid through the valve port 41, pulling it open. When the heat is again removed, the valve 40 is locked into its open position.

Referring now to FIGS. 7A, 7B, and 7C, plan and cross-sectional views of an embodiment of the invention having a tricuspid catheter tip microvalve in an opened and closed state is shown. The microvalve is generally designated by the reference numeral 50. In this embodiment of the invention a tricuspid semi-toroidal structure is shown in which a passage 51 through the center is the fluidic port. The microvalve 50 has three substantially identical segments which form a cuspid valve formation similar to a heart valve to facilitate opening, closing and sealing of the valve. The microvalve 50 has an outer wall 52 that forms a ridge 53. The microvalve 50 also has an inner wall 54 adjacent the fluidic port 51. The inner wall 54 is constructed of a shape memory polymer (SMP).

The valve 50 is adapted to be attached to the end of a microcatheter as described earlier. When pressure is raised inside the catheter, fluid can flow out of the catheter through the valve 50 and when pressure is lowered inside the catheter fluid can flow into the catheter through the valve 50 as shown by the double headed arrow. The microvalve 50 is show in the open position in FIG. 7B and in the closed position in FIGS. 7A and 7C.

To actuate the microvalve 50, the SMP is heated with an accompanying pressure difference between the outside and inside of the valve 50. The valve 50 is closed by heating the inner wall 54, which is constructed of a shape memory polymer (SMP). The pressure inside the catheter is raised. This pressure causes the inner wall 54 of the valve to pinch-off sealing against fluid flow. The heat is then raised while pressure is still raised in order to set the polymer in its low temperature state. The valve 50 is now stable in its closed position. To open the valve 50, the SMP is once again heated and the pressure inside the catheter is lowered. This forces fluid through the valve port 51, pulling it open. When the heat is again removed, the valve 50 is locked into its open position.

Referring now to FIGS. 8A and 8B, a MEMS-based microvalve 60 made with a SMP flap 63 attached to a micromachined substrate 62 is shown. The microvalve is constructed planar using microfluidics based on silicon integrated circuit and MEMS technology. These tiny valves are fabricated using microfabrication techniques. Using this method, valves can be made of varying thickness down to the order of 10 microns and varying diameter to fit onto the end of any catheter. The flap 63 is constructed from a shape memory material such as a shape memory polymer (SMP) film. The shape memory material could be other materials for example it could be a shape memory alloy. The flap 63 is attached to the substrate 62 and includes a flapper section 64. When closed the flapper section 64 overlaps assuring a fluid tight closure.

The flap 53 is connected to the body 62 of the valve 60 and adapted to move from an open position to a closed position. With the flap 63 frozen in the open position shape, flow 65 can occur in either direction. This allows controlled release of a substance into a desired location or the collection of a sample from a desired location. The check valve 60 will only open or close during applied heat and pressure. Raising the temperature of the SMP above the glass transition temperature softens the material and allows it to easily deform under the pressure around it. If the applied pressure remains and the heat source is removed, the SMP becomes rigid and holds the shape that was imposed by the pressurization. When pressure is removed, the SMP structure tends to hold a similar shape, thus keeping the valve opened or closed. Reversing the pressure bias while the SMP is rigid will not reverse the opened or closed state of the valve.

Various embodiments of a bistable microvalve and microcatheter system having been described, a shape memory material, specifically a shape memory polymer (SMP), and heat transfer system constructed in accordance with the present invention will now be described. The shape memory polymer (SMP) system is a mechanical system that when actuated will open or close the central passage in the bistable valve. An optical source provides light energy through the optical fiber. The optical fiber is often sheathed in a buffer jacket with additional material layers built up to form a biocompatible catheter. The fiber is multimode with typical core dimensions between 50–1000 µm. The distal end of the fiber delivers light to the shape memory polymer (SMP).

The optical source can be a light source coupled into an optical fiber. The light is radiated from the light source. The light is transmitted by the optical fiber to the shape memory material. The optical source can be various systems. For example, the optical source can be heated as described in U.S. Pat. No. 6,102,917, by Maitland et al, patented Aug. 15, 2000, as follows: "The catheter section, extension section, and control unit are interconnected by optic fiber connectors. Control unit includes a laser, laser control or driving electronics and display panel assembly and connected to lase. Laser is connected by optic fibers via an optic fiber connector to a fiber optic coupler, such as a conventional 90/10 optical coupler, which is connected via an optic fiber to optic fiber connector. Coupler, wherein 90 percent of the light passes through and 10 percent is bypassed, is also connected by an optic fiber to a sensing photodetector, which is connected to the display panel section of assembly. Coupler is also connected by an optic fiber to a source photodetector, which is connected to the driving electronics or control section of assembly. Laser light (pulsed or continuous) from laser is transmitted by pulses through optic fiber, connector, optic fiber, coupler, optic fiber, connector, an optic fiber in extension section, connector, and an optic fiber in catheter section onto an end section of SMP microgripper, which retains the coil, causing heating of the material of microgripper located around the coil" The disclosure of U.S. Pat. No. 6,102,917 is incorporated herein by reference.

SMP materials are well known. For example, U.S. Pat. No. 6,086,599 for micro devices using shape memory polymer patches for mated connections, by Lee et al, patented Jul. 11, 2000, states: "SMP material is known in the art, and has been recently utilized as delivery means for medical or non-medical devices to inaccessible locations, such as blood vessels or inside a machine or tubing system." U.S. Pat. No. 5,911,737 for microfabricated therapeutic actuators, by Lee et al, patented Jun. 15, 1999 describes a SMP material as follows: "The SMP material, a polyurethane-based material that undergoes a phase transformation at a temperature (Tg). The SMP material can be constructed so as to be inert to any fluids of the human body, for example, and can be constructed to be responsive to various desired phase transformation temperatures, Tg, above which the material is soft and reshapable and then by cooling the material below the Tg, the material retains the reshaped configuration until it is again heated to above the Tg temperature at which time the SMP material returns to its original memory shape." U.S. Pat. No. 6,102,917 for a shape memory polymer (SMP) gripper with a release sensing system, by Maitland et al, patented Aug. 15, 2000, describes a SMP material as follows: "SMP, a polyurethane-based material that undergoes a phase transformation at a temperature (Tg) of choice.

After the material is polymerized (cross-linked), the material is molded into its memory shape. At temperatures above Tg, the material can be easily reshaped into another configuration, and upon cooling below the Tg the new shape is fixed, but upon increasing the temperature to above the Tg, the material will return to its original memory shape." U.S. Pat. No. 5,189,110 for a shape memory polymer resin, composition and the shape memorizing molded product thereof, by Ikematu et al, patented Feb. 23, 1993, provides the following description: A shape memory polymer resin, consisting essentially of a block copolymer having an A-B-A block structure in the polymer chain, and having an average molecular weight within the range of 10,000 to 1,000,000, wherein (a) block A is a polymer block comprising a homopolymer or a copolymer of a vinyl aromatic compound and/or a hydrogenated product thereof; (b) block B is a polymer block comprising a homopolymer or a copolymer of butadiene and/or a hydrogenated product thereof, the content of butadiene and/or the hydrogenated product thereof in block B being at least 80% by weight, and 80 to 91% of the linkages of the butadiene and/or the hydrogenated product thereof being 1,4-linkages; (c) at least 80% by weight of the conjugated diene in the block copolymer being hydrogenated; and (d) the block copolymer comprises 5 to 50% by weight of said block A; and a shape memory resin composition and a shape memorizing molded product thereof." The patents identified in this paragraph are incorporated herein by reference.

SMP actuation is based on the unique property of the shape memory polymer. This polymer possesses a glass transformation temperature ($T_g$) above which the material enters a reversible rubbery state where it becomes soft and flexible and easy to reshape the material. Once cooled below $T_g$, the shape is frozen in place by the material's glassy state and the material becomes hardened to over 200 times the elastic modulus of the rubbery state. The reshaped SMP can be used to hold its shape until it is intentionally relaxed by heating the SMP above $T_g$ again in absence of excessive loading.

The system uses energy in the form of light guided by an optical fiber that radiates the light into the shape memory polymer. The light is absorbed by the shape memory polymer and converted into heat. The shape memory polymer will change stiffness when heated above a transition temperature. When light from the diffusing chamber is absorbed in the SMP the polymer is heated and the proximal end relaxes to its primary shape. The primary shape of the SMP is formed by heating the SMP above its melting temperature as in extrusion or molding processes. The SMP can be made by mold injection under vacuum.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A bistable valve and catheter apparatus, comprising:
   a catheter,
   a bistable valve body operatively connected to said catheter, said bistable valve body having a passage wherein said bistable valve body is generally circular in shape and said passage extends through said bistable valve body at approximately the center of said generally circular shape bistable valve body,
   said bistable valve body including a shape memory material adapted to move from a first shape wherein said passage is restricted to a second and different shape wherein said passage is open, and
   a mechanism operatively connected to said bistable valve body, adapted to cause said shape memory material to be moved from said first shape to said second shape.

2. The bistable valve and catheter apparatus of claim 1 wherein said catheter is a microcatheter.

3. The bistable valve and catheter apparatus of claim 1 wherein said catheter is a microcatheter and said bistable valve body is a microvalve.

4. The bistable valve and catheter apparatus of claim 1 wherein said bistable valve body is a microvalve.

5. The bistable valve and catheter apparatus of claim 1 wherein said shape memory material is a shape memory polymer.

6. The bistable valve and catheter apparatus of claim 5 wherein said shape memory polymer possesses a glass transformation temperature ($T_g$) above which the material enters a reversible rubbery state where it becomes soft and flexible and easy to reshape the material and will return to its primary shape if not subjected to undue pressure and once cooled below $T_g$, the shape is frozen in place and the material becomes hardened and will hold its shape until it is intentionally relaxed by heating the SMP above $T_g$ in absence of excessive loading.

7. The bistable valve and catheter apparatus of claim 1 wherein said shape memory material is a shape memory alloy.

8. A bistable valve and catheter apparatus, comprising:
 a catheter,
 a bistable valve body operatively connected to said catheter, said bistable valve body having a passage, wherein said bistable valve body is generally circular in shape and said passage extends through said bistable valve body at approximately the center of said generally circular shape bistable valve body,
 said bistable valve body including a shape memory material adapted to move from a first shape wherein said passage is open to a second and different shape wherein said passage is restricted, wherein said shape memory material is located around said passage, and
 a mechanism operatively connected to said bistable valve body, adapted to cause said shape memory material to be moved from said first shape to said second shape.

9. The bistable valve and catheter apparatus of claim 8 wherein said mechanism operatively connected to said bistable valve body, adapted to cause said shape memory material to be moved from said first shape to said second shape includes a heat transfer mechanism and a pressure transfer mechanism.

10. The bistable valve and catheter apparatus of claim 8 wherein said heat transfer mechanism includes an optical fiber.

11. The bistable valve and catheter apparatus of claim 8 wherein said heat transfer mechanism includes an optical fiber for transmitting laser light and transmitting and receiving diagnostic signals.

12. The bistable valve and catheter apparatus of claim 8 wherein said heat transfer mechanism includes induced resistive heating by an external wave field, such as by an associated magnetic or radio frequency (RF) source.

13. The bistable valve and catheter apparatus of claim 8 wherein said heat transfer mechanism includes direct resistive heating by electrical leads attached to said valve.

14. The bistable valve and catheter apparatus of claim 8 wherein said heat transfer mechanism includes external heating carried out through electrical induction or electrothermal heating.

* * * * *